(12) United States Patent
Matsuo et al.

(10) Patent No.: US 7,101,533 B2
(45) Date of Patent: Sep. 5, 2006

(54) AGENT FOR INDUCING RECEPTOR POTENTIAL

(75) Inventors: Toshihiko Matsuo, Okayama (JP); Yasufumi Dan-Oh, Okayama (JP); Sadaharu Suga, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 93 days.

(21) Appl. No.: 10/673,487

(22) Filed: Sep. 30, 2003

(65) Prior Publication Data

US 2004/0062713 A1 Apr. 1, 2004

(30) Foreign Application Priority Data

Sep. 30, 2002 (JP) .............................. 2002-285784

(51) Int. Cl.
*A61B 10/00* (2006.01)

(52) U.S. Cl. .................... 424/9.6; 548/150; 548/365.1; 546/210

(58) Field of Classification Search ................ 548/150, 548/365.1; 546/210; 514/366, 407; 424/9.6
See application file for complete search history.

(56) References Cited

U.S. PATENT DOCUMENTS 5,132,095 A * 7/1992 Koshiishi et al. ......... 422/82.07

FOREIGN PATENT DOCUMENTS

| JP | 511697/96 | 12/1996 |
| JP | 506662/99 | 6/1999 |
| WO | WO 94/26209 | 11/1994 |
| WO | WO 96/39221 | 12/1996 |

OTHER PUBLICATIONS

Momose-Sato et al., Journal of Membrane Biology, (1999), 172(2), 145-157.*
Momose et al., 1999, CAS: 132:90253.*
KANKO-SHIKISO (*Photosynthetic Dyes*), ed. Masaaki Hayami, (Sangyo Tosho Publishers, Oct. 17, 1997).
JIKKEN-IGAKU, (Experimental Medicine), vol. 7, No. 6, Apr. 5, 1999, (Yodosha, Co., Ltd., Tokyo, Japan), p. 91-97.

* cited by examiner

*Primary Examiner*—Kamal A. Saeed
*Assistant Examiner*—Robert Shiao
(74) *Attorney, Agent, or Firm*—Browdy and Neimark, PLLC

(57) ABSTRACT

Disclosed is an agent for inducing receptor potential, which comprises an organic dye compound capable of inducing/evoking receptor potential in response to photostimulation in the optic nerve, wherein the organic dye compound is a polymethine organic dye compound. Also disclosed is a substituent material for the retina comprising the agent.

2 Claims, No Drawings

AGENT FOR INDUCING RECEPTOR POTENTIAL

BACKGROUND OF THE INVENTION

1. Field of the Invention

The present invention relates to a use of organic dye compounds, more particularly, to an agent for inducing receptor potential, which comprises an organic dye compound(s) capable of inducing/evoking a receptor potential in response to photostimulation.

2. Description of the Prior Art

As it is well known that vision is established through sequential processes of conversion of photostimulation received from an object by the eye into electric energy; the resulting electric energy's transmission to the brain; and the brain's recognition and judgement of the color and shape of the object. Photostimulation received by the eye is converted into electric energy in the retina, and when photostimulation with a level exceeding the threshold of visual cell receptors is focused on the retina, a receptor potential is evoked in the optic nerve and then transmitted to the upper central nervous system in an impulse form. The retinal function of converting photostimulation into electric energy is quite important for establishing vision. The retinal damage induced by injuries or diseases may result in visual disorders such as narrowing of visual field, reduction of visual acuity, and nyctalopia.

At present, in Japan, it is said there are millions of patients suffering from visual disorders such as narrowing of visual field caused by retinal disorders, reduction of visual acuity, and nyctalopia. The retinal disorders are mostly evoked by diseases such as retinitis pigmentosa, age-related macular degeneration, and diabetic retinopathy. For instance, referring to retinitis pigmentosa which is an intractable disease specified as a specific disease by the Ministry of Health, Labor and Welfare of Japan, congenital disposition deteriorates retinal cells to evoke visual field scotomas, and this results in blindness after gradual progression. However, even when the retina is suffers from any disorder and, for example, in retinitis pigmentosa in which the damage only stays in visual cells so as to keep the optic nerve substantially normal conditions, artificial installation of devices for converting photostimulation into electric signals and transmitting them to the optic nerve would brighten the visual field, meaning that it would possibly improve "the quality of life".

Now, in this field, there have been energetically progressed researches on substituent materials for the retina such as "artificial retinae" where a photosensor, mainly composed of a photoelectric-converting device such as a charge-coupled device (CCD), is formed into a chip which is then embedded in the eyeball as disclosed, for example, in Japanese Patent Kohyo Nos. 511,697/96 and 506,662/99. Since conventionally proposed artificial retinae would have difficulties in miniaturizing both photosensors and external power supplies for actuating the photosensors, it is clear that there still remain hurdles to be overcome until actual exploitation of a device that can be inserted into the eyeball for use.

SUMMARY OF THE INVENTION

The present invention provides an organic chemical material capable of effectively evoking receptor potential in response to photostimulation in the optic nerve, and uses thereof.

The present inventors focused on organic dye compounds capable of absorbing light (hereinafter designated as "light-absorbing organic dye compounds") and eagerly studied and screened them. As a result, they made a novel finding that some of the light-absorbing organic dye compounds, including polymethine dyes, evoke receptor potential in response to photostimulation in animal optic nerves, particularly, their retinal nerve cells that constitute the optic nerve. They also found that an agent for evoking receptor potential, which comprises any of these light-absorbing organic dye compounds, can be advantageously used as a substituent material for vision-related substances, i.e., a substituent material for the retina.

Thus, the present invention solves the above object by providing an agent for evoking receptor potential, which comprises an organic dye compound capable of evoking receptor potential in response to photostimulation.

Also the present invention solves the above object by providing a substituent material for the retina using the agent.

DETAILED DESCRIPTION OF THE INVENTION

The term "organic dye compounds" as referred to as in the present invention means organic dye compounds in general which evoke receptor potential in response to photostimulation in the optic nerve, particularly, those which have an absorption maximum wavelength in the visible region and evoke receptor potential in response to photostimulation in the optic nerve, particularly, retinal nerve cells which constitute the optic nerve when they receive visible lights. Any organic dye compounds with any structure can be arbitrarily used in the present invention as long as they absorb visible light and evoke receptor potential in response to photostimulation in the optic nerve. Examples of such organic dye compounds are those which absorb light in the blue, green and/or red regions in the visible region; acridine, azanulene, azo, anthraquinone, indigo, indanthlene, oxadine, xanthene, coumarin, dioxadine, thiazine, thioindigo, tetraporphyradine, triphenylmethane, triphenothiadine, naphthoquinone, phthalocyanine, benzoquinone, benzopyran, benzofuranone, polymethine, porphyrin, and rhodamine organic dye compounds.

Preferable among the above organic dye compounds are polymethine organic dye compounds such as oxanol, cyanine, styryl, merocyanine, and rhodacyanine dyes, which are coupled with the same or different cyclic cores such as imidazole, indanedione, indolenine, oxazole, quinoline, selenazole, thiazoline, thiazole, thioxazolidone, thionaphtene, thiobarbituric acid, thiohydantoine, naphthoxazole, naphthoselenazole, naphthothiazole, pyrazolone, pyridine, benzimidazole, benzoindolenine, benzooxazole, bezoselenazole, benzothiazole, and rhodanine rings, comprising polymethine chains such as dimethine, trimethine, tetramethine, pentamethine, hexamethine, and heptamethine having (i) one or more substituents such as aliphatic hydrocarbon groups such as methyl, ethyl, propyl, and isopropyl groups; alicyclic hydrocarbon groups such as cyclopropyl, cyclobutyl, cyclopenthyl, cyclohexyl, and cyclohexenyl groups; aromatic hydrocarbon groups such as phenyl and biphenyl groups; and halogens such as fluoro, chloro, bromo, and iodine groups; and (ii) having at both ends one or more groups of aliphatic hydrocarbon groups such as methyl, ethyl, propyl, isopropyl, 1-propenyl, 2-propenyl, butyl, isobutyl, sec-butyl, tert-butyl, 2-butenyl, 1,3-butadienyl, pentenyl, isopentyl, neopentyl, tert-pentyl, 1-methylpentyl, 2-methylpentyl, 2-pentenyl, hexyl, isohexyl groups; aliphatic hydrocarbon groups such as cyclopropyl, cyclobutyl, cyclopentyl, and cyclohexyl groups; aromatic hydrocarbons such as phenyl group; ether groups such as methoxy, ethoxy, and propoxy groups; ester groups such as acetoxy, benzoyloxy, methoxycarbonyl, ethoxycarbonyl, and propoxycarbonyl groups; amino groups such as methyl amino, dimethyl amino, ethyl amino, diethyl amino, propyl amino, dipropyl amino, butyl amino, and dibutyl amino groups; hydroxyl, carboxyl, sulfo, nitro, and cyano groups; and combinations thereof. Among these organic dye compounds, those which absorb light in the blue, green and/or red regions of visible light are most preferably used. Examples of the counter ions in the polymethine organic dye compounds are selected, for example, from anions such as chlorine, bromine, and iodine ions; and cations such as ammonium, trimethyl ammonium, and triethyl ammonium ions, however, the polymethine organic dye compounds do not have any counter ion when they have a negatively or positively charged substituent intramolecularly.

Concrete examples of such organic dye compounds are, for example, those represented by Chemical Formulae 1 to 17. It is said that the process of photoelectric conversion in vivo is proceeded through the cis-trans isomerization of visual pigments evoked by photostimulation. Also, in conventional substituent materials for the retina, there have been made trials of selecting compounds that can be cis-trans isomerized by photostimulation, however, all the above compounds are not cis-trans isomerized even when irradiated. The present invention is to reveal the fact that even a compound that does not evoke cis-trans isomerization when irradiated can be used as a substituent material for the retina.

Chemical Formula 1:

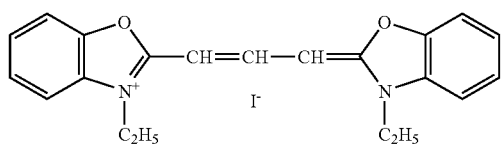

Chemical Formula 2:

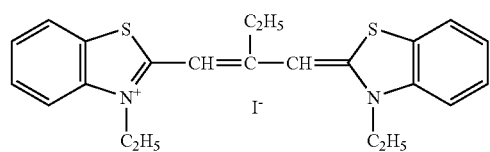

Chemical Formula 3:

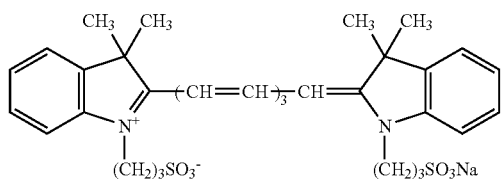

Chemical Formula 4:

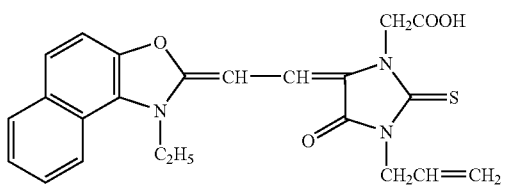

Chemical Formula 5:

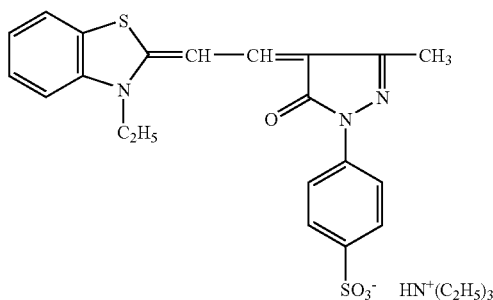

Chemical Formula 6:

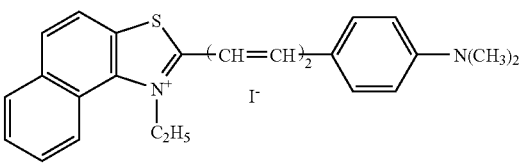

Chemical Formula 7:

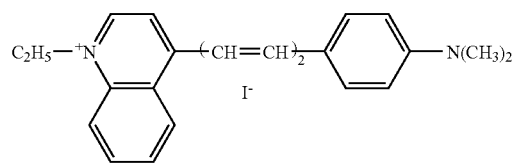

Chemical Formula 8:

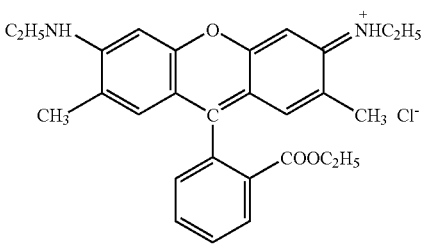

Chemical Formula 9:

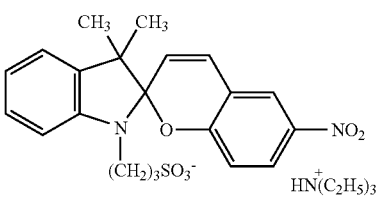

Chemical Formula 10:

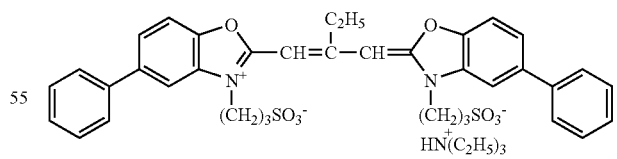

Chemical Formula 11:

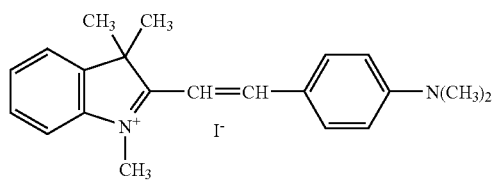

-continued

Chemical Formula 12:

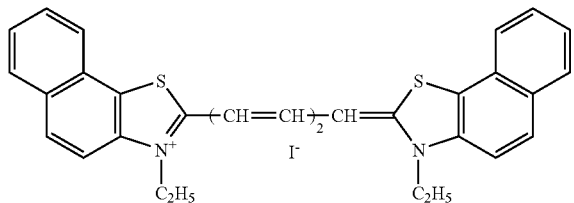

Chemical Formula 13:

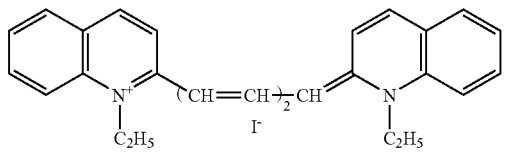

Chemical Formula 14:

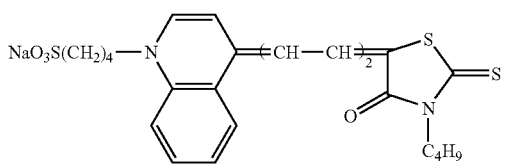

Chemical Formula 15:

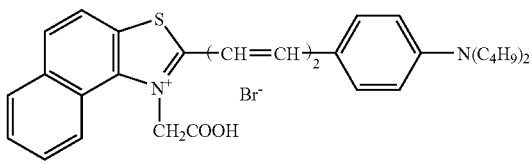

Chemical Formula 16:

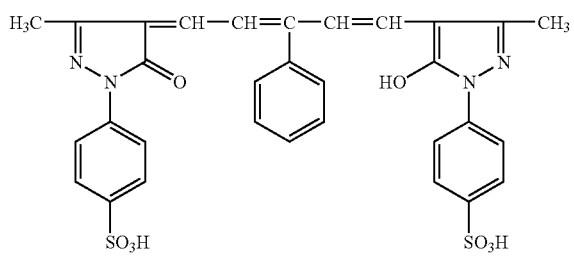

Chemical Formula 17:

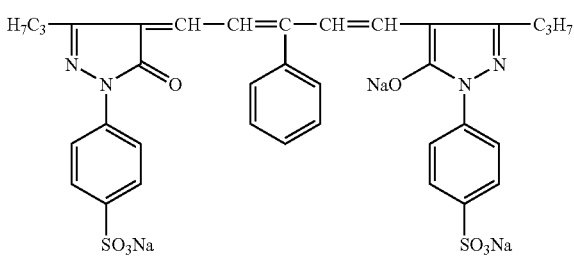

All the above polymethine organic dye compounds can be obtained in the desired amount either by the method disclosed in "Kanko-Shikiso" (Photosynthetic Dyes), pp. 11–31, edited by Masaaki Hayami, published by Sangyo Tosho Publisher on Oct. 17, 1997; or in accordance therewith. In case the compounds are commercially available, they can be optionally purified prior to use. Evaluation of whether organic dye compounds evoke receptor potential in response to photostimulation in the optic nerve can be determined in accordance with the intracellular calcium experiment method disclosed in "Jikken-Igaku" (Experimental Medicine), Vol. 7, No. 6, edited by Hideaki Karaki et al., published on Apr. 5, 1989 by Yodosha, Co., Ltd., Tokyo, Japan, with a modification that an organic dye compound to be tested coexists in animal retinal cells cultured in a nutrient culture medium containing a fluorescent calcium indicator, followed by detecting the intensity of fluorescence emitted from the indicator or of the electric potential generated intracellularly.

The term "agent for evoking receptor potential" as referred to as in the present invention means a composition comprising one or more of the above-identified organic dye compounds depending on use. Within the scope of the present invention, the above agent for evoking receptor potential of the present invention may further contain one or more other ingredients selected from ophthalmic agents, excipients, solvents, stabilizers, antioxidants, and other ophthalmologically acceptable preparations and carriers. Depending on use, when the agent for evoking receptor potential of the present invention is applied, as a substituent material for the retina, to patients with visual disorders or dyschromatopsia, a plurality of the organic dye compounds, having each different absorption maxima in the visible region, are preferably used in combination to allow the compounds, which function as the main components of the agent, to exert an absorption ability through over the visible region as a whole.

Explaining the use of the agent for evoking receptor potential of the present invention, as described above, since the organic dye compounds have a property of evoking receptor potential in response to photostimulation in nerve cells, they can be advantageously used as materials for preparing substituent materials for the retina, which are directed to ameliorate or even cure visual disorders induced by injuries or diseases, dyschromatopsia induced by injuries, diseases, or congenital dispositions, particularly, they can be quite advantageously used as substituent materials for visual-related substances.

The term "substituent materials for the retina" as referred to as in the present invention means artificial materials substitutable for a part or the whole of the function of the retinae of animals including humans. Concrete examples of such are those for visual-related substances, which can be, for example, introduced into the eyeball by injections, etc., after prepared into a solution form using solvents such as water, ethanol, dimethylsulfoxide, or a mixture thereof, which pharmacologically accept the agent for evoking receptor potential of the present invention; or which can be formed into artificial retinas by adhering the organic dye compound(s), as the main ingredients of materials for receptor potential, to insoluble materials, and installing and transplanting the resultants in the eyeball by means of surgeries, etc., to place them on the surface of the retina.

Examples of the above-identified former type of substituent materials for the retina are those which can be prepared by chemically binding a ligand specific to the receptor of retina to the organic dye compound(s), and injecting the resultant into the eyeball to allow the organic dye compound(s) to specifically bind to the surface of the retina, after being prepared in solution form. In this case, examples of such a ligand include visual-related substances, receptor proteins or antibodies against channel proteins, antibodies against receptor proteins, antibodies against membrane proteins, and fragments thereof.

Examples of the above-identified latter type of substituent materials for the retina are those prepared by using, as a base, biocompatible high molecules which are appropriately formed in the form of a film, sheet, or net to meet the shape and size of the optic cup or affected parts, and by chemically binding the agent for evoking receptor potential of the present invention to either or both of the surfaces of the base to allow the organic dye compound(s) to substantially contact with the intraocular solution; or those prepared by forming biocompatible high molecules, incorporated with the agent for evoking receptor potential of the present invention, to form the above-mentioned film, sheet, or net.

The above biocompatible high molecules used as the base in the present invention are not specifically restricted as long as they have an adequate hydrophilicity/hydrophobicity, rigidity, and flexibility; have a substantial transparency through over the visible region; and have an adequate tolerance to tear and in vivo enzymes. Examples of such biocompatible high molecules include those which are transplantable into the eyeball, for example, natural high molecules such as collagen, gelatin, cellulose, and hyaluronic acid; semisynthetic high molecules such as cross-linked products and derivatives of dextran, cellulose, pullulan, and heparin; synthetic high molecules including polymers and copolymers of silicon, polyacrylamide, polyacrylonitrile, polyacrylate, polyurea, polyurethane, polyester, polyethylene, polyethylene oxide, polyethylene glycol, polycarbonate, polycarbamate, poly(vinyl acetate), polyhydroxyalkylmethacrylate, poly(vinyl alcohol), poly(vinyl pyrrolidone), and polymethacrylate; and complexes thereof. In the case of transplanting a base coupled with the organic dye compound(s) to the surface of the retina and when the retina inevitably contacts with the base's surface not coupled with the organic dye compound(s), the base should preferably be selected from electroconductive biocompatible-high-molecules.

Methods to bind the agent for evoking receptor potential of the present invention to a base include, for example, those of directly reacting high molecules as the main constituents of the base with the organic dye compound(s) as the main constituent of the agent, or those of coupling the organic dye compound(s) with biocompatible high molecules using polyfunctional reagents having a plurality of active functional groups such as azlactone, amino, aldehyde, isocyanate, ethylene imino, epoxy, ketene, acid azide, acid hydrazide, acid anhydride, sulfonate, sulfonic acid halide, thioisocyanate, hydroxamic acid, vinyl, mercapto, and lactone groups.

Since the organic dye compounds can be used in such a manner of allowing them to contact with living bodies even though any of the above methods is employed, organic dye compounds with lesser side effects should preferably be selected for use. Among such organic dye compounds, for example, the above-mentioned polymethine organic dye compounds do not generally have toxicity such as cytotoxicity and merely have an extremely lower toxicity, and this facilitates the present invention.

Examples of diseases, to which the substituent materials for the retina of the present invention are applicable, are, for example, visual disorders such as narrowing of visual field, visual reduction, and nyctalopia that accompany diseases such as retinitis pigmentosa, age-related macular degeneration, and diabetic retinopathy; and dyschromatopsia evoked by the deficiency of specific retinal cones of the retinae in patients with dichromatism and anomalous trichromatism, drug intoxication, visual central neuropathy, and retinal diseases. The substituent materials can be advantageously used as medical materials for ameliorating or curing these visual disorders and dyschromatopsia. The agent for evoking receptor potential of the present invention is also useful in the field of optoelectronics in addition to the medical field; it is useful as a material for composing optical sensors in regulators, etc.

The following example explains a preferred embodiment according to the present invention:

EXAMPLE

Agent for Evoking Receptor Potential

Four compounds in Table 1 as polymethine organic dye compounds were examined whether they had any potential of evoking receptor potential in accordance with the intracellular calcium experimental method disclosed in "Jikken-Igaku" (Experimental Medicine), Vol. 7, No. 6, edited by Yuko Ichinohe, published on Apr. 5, 1989. The organic dye compounds represented by Chemical Formulae 14 to 17 are commercialized by Hayashibara Biochemical Laboratories Inc., Okayama, Japan, under the trade names of "NK-2761", "NK-5962", "NK-3041", and "NK-3630", respectively.

TABLE 1

| Organic dye compound | Fluorescent intensity | | Intracellular potential |
|---|---|---|---|
| | Without calcicludine | With calcicludine | |
| Chemical Formula 14 | Increased | Unchanged | Detected |
| Chemical Formula 15 | Increased | Unchanged | Detected |
| Chemical Formula 16 | Increased | Unchanged | Detected |
| Chemical Formula 17 | Increased | Unchanged | Detected |

After 10-day-old fertilized eggs were sterilized with 70% (v/v) aqueous ethanol solution, the shells were perforated to make a small hole in each egg, followed by extracting chick embryos therefrom. The eyeballs were extracted from the embryos and respectively halved by cutting down at their middle parts. The former aliquot in each eyeball was removed along with its vitreous body, followed by detaching the retina and dispersing the retinal cells by soaking in Hanks' solution (pH 7.4) containing 0.25% (w/v) trypsin and 1 mM ethylenediaminetetraacetic acid but not $Ca^{2+}$/$Mg^{2+}$. The dispersed retinal cells were centrifugally collected, washed with Dulbecco's Modified Eagle Medium (pH 7.4), suspended in Dulbecco's Modified Eagle Medium (pH 7.4) supplemented with 0.1 mg/ml streptomycin and 0.1 mg/ml ampicillin, seeded in 24-well culture plates at a cell density of $6\times10^5$ cells/ml, and cultured until the retinal nerve cells for constructing the optic nerve predominantly grew while replacing the culture medium with fresh one.

Thereafter, Fluo-4 acetoxymethyl ester, commercialized by Molecular Probe, Oregon, U.S.A., a fluorescent calcium indicator, was added to each well of the culture plates to give a concentration of 10 μM, incubated at 37° C. for 30 min, and further incubated for another 30 min similarly as above except for omitting Fluo-4 acetoxymethyl ester. Then, the culture medium in each well was replaced with a physiological saline (pH 7.4) containing 10 mM N-2-hydroxyethylpiperadine-N'-2-ethanesulfonate, 145 mM sodium chloride, 5 mM potassium chloride, 10 mM magnesium chloride, 1 mM calcium chloride, and 10 mM glucose. Each culture plate was placed on the stage of an inverted microscope installed in a commercially available intracellular calcium microscopic measurement apparatus. The organic dye compounds in Table 1 were respectively dissolved in dimethylsulfoxide and irradiated with a light having a wavelength of 470 to 490 nm to excite Fluo-4 acetoxymethyl ester before or after being added to each culture in each well to give a concentration of 0.0005 to 0.5 µg/ml, followed by detecting the intensity of fluorescence and the intracellular potential at a wavelength of around 510 to 550 nm emitted from the excited Fluo-4 acetoxymethyl ester.

As evident from the results in Table 1, all the tested four types of organic dye compounds, represented by Chemical Formulae 14 to 17 that significantly increased the intensity of fluorescence emitted from Fluo-4 acetoxymethyl ester. In the systems with any of the compounds represented by Chemical Formulae 14 to 17, a significant receptor potential was observed as an intracellular potential. While in the systems that had been tested similarly as above except for adding to each culture 2.5 µM of calcicludine as an antagonist against L-, N-, and P-types of high-threshold calcium channels, there were observed neither intracellular potential nor increase of the intensity of fluorescence emitted from Fluo-4 acetoxymethyl ester.

When Fluo-4 acetoxymethyl ester is irradiated after being allowed to be taken up by nerve cells, it fluoresces at a wavelength of around 510 to 550 nm only when calcium ions flow into the nerve cells. Since it is well known that the induction of receptor potential in the optic nerve opens the calcium channels of cells and allows calcium ions to flow into the cells, the fact that the intensity of fluorescence from Fluo-4 acetoxymethyl ester was increased only in the presence of any of the organic dye compounds, represented by Chemical Formulae 14 to 17, indicates that the compounds have a property of evoking receptor potential in response to photostimulation in the optic nerve. The above conclusion was also evidenced by the fact that a significant intracellular potential was observed in the absence of calcicludine.

Vision is established in the optic nerve through the naturally-occurring processes of chemical reactions of visual-related substances such as rhodopsin, G-protein, cyclic GMP, and phosphodiesterase to evoke receptor potential in response to photostimulation. The results in this example indicates that the light-absorbing organic dye compounds, particularly, polymethine organic dye compounds have a property of evoking receptor potential in response to photostimulation in the optic nerve, particularly, retinal nerve cells which constitute the optic nerve, meaning that the agent for evoking receptor potential, which comprises the above-identified organic dye compound(s), is useful as a material for substituting visual-related substances in substituent materials for the retina.

As described above, the present invention was made based on a self-finding by the present inventors that, among light-absorbing organic dye compounds, there exist compounds that evoke receptor potential in response to photostimulation in the optic nerve. The agent comprising such an organic dye compound(s) of the present invention is significantly useful as a substituent material for visual-related substances in substituent materials for the retina, including artificial membranes directed to ameliorate or even cure visual disorders caused by retinal disorders such as narrowing of visual field, reduction of visual acuity, and nyctalopia induced by injuries and diseases; and dyschromatopsia caused by drug intoxication, nerve disorders of visual center, retinal diseases, and deficiency of specific retinal cones.

The present invention with such an outstanding effect is a significantly important invention that greatly contributes to this art.

While there has been described what is at present considered to be the preferred embodiments of the invention, it will be understood the various modifications may be made therein, and it is intended to cover the appended claims all such modifications as fall within the true spirits and scope of the invention.

We claim:

1. An ophthalmologically acceptable artificial retinal material in the form of a film, sheet or net to meet the shape and size of the optic cup or affected parts, which can be installed in or transplanted into an eyeball surgically and which material can be substituted for a part or the whole of the function of the retinae of animals including humans, which is directed to ameliorate or cure visual disorders caused by retinal disorders and which consists essentially of a biocompatible large molecule as an ophthalmologically acceptable base to which an ophthalmologically acceptable organic dye compound is chemically bound or incorporated, said organic dye compound having an absorption maximum in the visible region and being capable of evoking a receptor potential in response to photostimulation in an optic nerve, said biocompatible large molecule having an adequate hydrophilicity/hydrophobicity, rigidity, flexibility, and electroconductivity and being a member selected from the group consisting of (a) natural large molecules selected from the group consisting of collagen, gelatin, cellulose, and hyaluronic acid; (b) cross-linked products and derivatives of dextran, cellulose, pullulan, and heparin; (c) synthetic large molecules selected from the group consisting of polymers and copolymers of silicon, polyacrylamide, polyacrylonitrile, polyacrylate, polyurea, polyurethane, polyester, polyethylene, polyethylene oxide, polyethylene glycol, polycarbonate, polycarbamate, poly(vinyl acetate), polyhydroxyalkylmethacrylate, poly(vinyl alcohol), poly (vinyl pyrrolidone), and polymethacrylate; and (d) a complex thereof.

2. The artificial material of claim 1, wherein said organic dye compound is a polymethine organic dye compound.

* * * * *